US008001442B2

(12) United States Patent
Munetaka

(10) Patent No.: US 8,001,442 B2
(45) Date of Patent: Aug. 16, 2011

(54) DATA-PROCESSING SYSTEM FOR MEASUREMENT DEVICES

(75) Inventor: Keisuke Munetaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1284 days.

(21) Appl. No.: 11/635,048

(22) Filed: Dec. 7, 2006

(65) Prior Publication Data

US 2007/0150785 A1      Jun. 28, 2007

(30) Foreign Application Priority Data

Dec. 9, 2005  (JP) ................................ 2005-355499

(51) Int. Cl.
*G11C 29/00* (2006.01)
(52) U.S. Cl. ...................................... 714/763
(58) Field of Classification Search .................. 714/763, 714/721, 712, 745, 799
See application file for complete search history.

(56) References Cited

U.S. PATENT DOCUMENTS 4,625,312 A * 11/1986 Bashaw .......................... 714/31
6,029,495 A    2/2000 Munetaka
6,650,409 B1 * 11/2003 Noguchi et al. ........... 356/237.3

FOREIGN PATENT DOCUMENTS

| JP | 2000-258421 A | 9/2000 |
|----|---------------|--------|
| JP | 2002-116211 A | 4/2002 |
| JP | 2003-057248 A | 2/2003 |
| JP | 2005-106669 A | 4/2005 |
| WO | WO 02-061514 A1 | 8/2002 |

OTHER PUBLICATIONS

Shimadzu North America, "GCsolution Software The Future Standard for Increased GC Productivity and Easy Operation".
Japanese Office Action dated Mar. 9, 2010, issued in corresponding Japanese Patent Application No. 2005-355499.

* cited by examiner

*Primary Examiner* — Guy J Lamarre
(74) *Attorney, Agent, or Firm* — Westerman, Hattori, Daniels & Adrian, LLP

(57) ABSTRACT

The present invention provides a data-processing system for measurement devices, which performs a step-by-step sequence of data-processing tasks. In a conventional data-processing system, a failure in one data-processing task also causes the subsequent tasks to be unsuccessful. In such a case, the conventional data-processing system indicates the result of each unsuccessful task or the final result of the analysis by displaying only a blank or a specific character (e.g. the digit "0"). From such simple information, users cannot immediately identify the cause of the error. In contrast, in the data-processing system according to the present invention, if a data-processing task has been incorrectly performed for some reason, an error detector detects the error, and an error investigator identifies the cause of the error. Then, an error message displayer prepares an error message indicating the reason why the data-processing task concerned was unsuccessful and then displays the error message as the result of each of the aforementioned task and the subsequent tasks. The user can immediately learn the cause of the error by checking the error message of any of the unsuccessful tasks. Thus, the problem can be identified and solved in a shorter period of time.

5 Claims, 2 Drawing Sheets

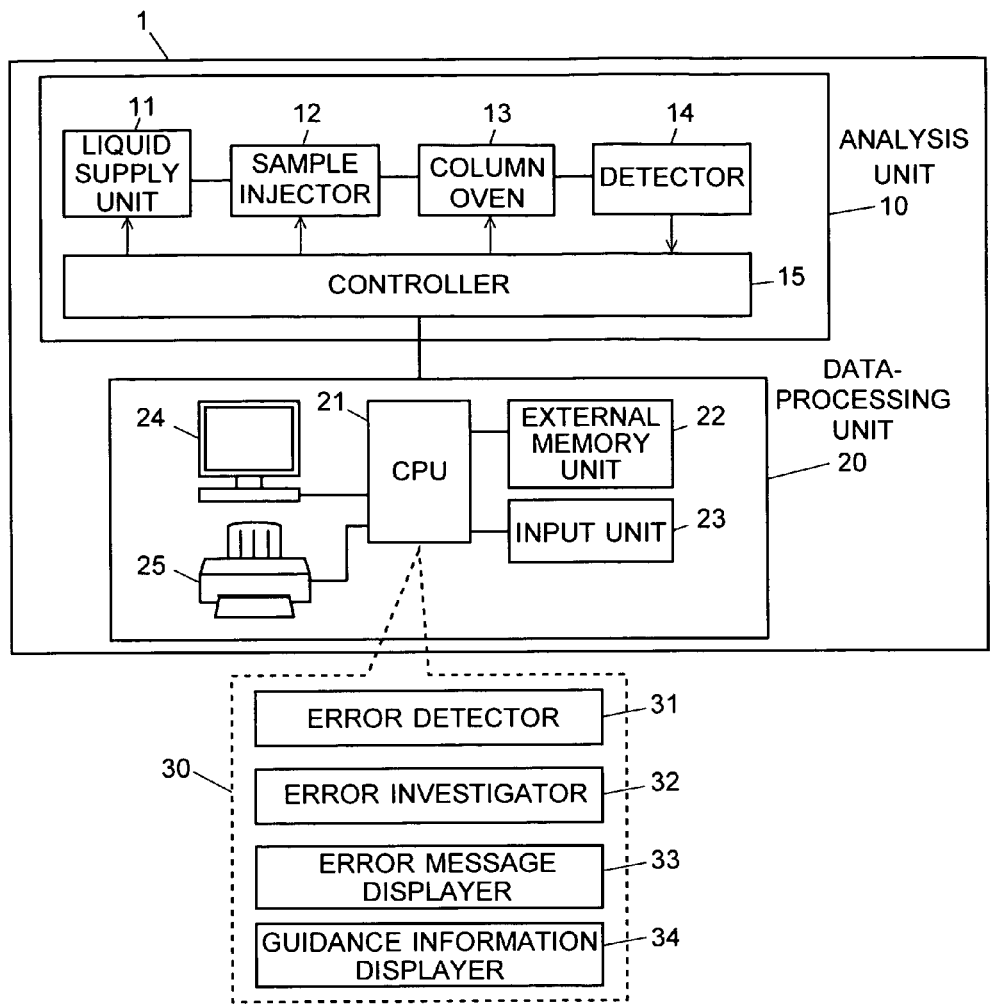

Fig. 3

| Analysis Error |
|---|
| Unable to calculate concentration because no calibration curve is prepared.<br>Possible reason(s):<br>• The operation necessary for creating a calibration curve using standard samples has not been finished.<br>   • Select <Batch Table> in <LC Postrun-analysis> to execute a batch process for creating a calibration curve.<br>     >>How to create a calibration curve by the batch process<br>   • Select <Calibration Curve> in <LC Postrun-analysis> to create a calibration curve.<br>     >> How to create a calibration curve through the Calibration Curve window<br>• In the course of the analysis using the standard samples, the calibration curve was not correctly created. |

Fig. 4

| ID | Compound Name | Retention Time | Area | Height | Concentration |
|---|---|---|---|---|---|
| 1 | Methyl_paraben | 2.660 | 175519 | 30759 | 0 |
| 2 | Ethyl_paraben | 0 | 0 | 0 | 0 |

DATA-PROCESSING SYSTEM FOR MEASUREMENT DEVICES

The present invention relates to a data-processing system having the functions of performing a step-by-step sequence of data-processing tasks and displaying the result of each task, on the basis of measurement data obtained with a measurement device, such as a liquid chromatograph, a gas chromatograph or a mass spectrometer. The present invention also relates to a program for operating a computer as the above data-processing system. In this specification, a "step-by-step" sequence is defined as a sequence of data-processing steps (or tasks) each of which uses the result of the previous step (or task), but not including the first step (or task).

BACKGROUND OF THE INVENTION

In recent years, many measurement devices, such as liquid chromatographs, perform not only measuring operations but also various kinds of data-processing operations using the data obtained from the measuring operations. Usually, a data-processing operation includes multiple tasks, e.g. peak integration, sample identification, calibration, quantitative determination, and statistical calculation, using a data-processing system that is built in or externally connected to the measurement device.

In many cases, the data-processing system for measurement devices consists of a computer on which a specific application program is running. An example of such application programs is disclosed in Non-Patent Document 1 described later.

During its operation, the data-processing system may encounter an abnormality or trouble that prevents the ongoing process from producing a correct result. If the data processing is performed on a step-by-step basis, a failure in one step also prevents the subsequent steps from producing correct results. In a conventional data-processing system, when a problem occurs in a certain step, the system displays a specific character (e.g. the digit "0") or a blank in each of the areas for showing the results of the aforementioned step and the subsequent steps, indicating that the system has failed to produce correct results.

FIG. 4 shows an example of a quantitative determination report containing some errors, produced by a conventional data-processing system. It shows that the concentration of Methyl_paraben of ID number 1 is zero, which contradicts the fact that the area and height of the peak are 175,519 and 30,759, respectively. This contradiction suggests that some problem has occurred in the analytical curve and/or the quantitative determination parameters used in the method used For Ethyl_paraben of ID number 2, the report indicates the retention time, the area and other values are zero. This result suggests that the chromatogram itself is incorrect or the peak integration method and/or the compound table has some problems.

[Non-Patent Document 1] "GCsolution Software/The Future Standard for Increased GC Productivity and Easy Operation", [online], Shimadzu Corporation, [Search Date: Nov. 13, 2006], Internet <http://www.ssi.shimadzu.com/products/product.cfm?product=gcsolution>

As shown in FIG. 4, if the report enumerates the results of a sequence of data-processing tasks on the same screen, the user can identify the step in which an error has occurred and make an estimation of the cause of the error.

In contrast, when the result of only one task is displayed on the screen, it is impossible to identify the step in which the error has occurred. For example, suppose that the system has obtained the results shown in FIG. 4 and is now showing only the value "0" of the "Area" for ID number 2. In this situation, the user can tell that some error has occurred but cannot immediately identify the step in which the error has taken place. Therefore, it is necessary to take the trouble of manually browsing through the results of the previous steps one after another.

In a measurement using a liquid chromatograph, it is common to continue the measurement for a long time while automatically exchanging a large number of samples one after another and performing a regular set of data-processing tasks for the measurement data of each sample. In such a long-time, automatic operation, the user rarely keeps watching the system on a continuous basis; he or she usually checks only the final result of the data-processing operation by printing out a report.

When a conventional data-processing system is used in this manner, if an error has occurred in a certain data-processing step and prevented the following process to be correctly performed, the printout of the report presents only the final, erroneous result, e.g. the digit "0". From this simple information, the user cannot identify the step in which the error has occurred. Therefore, he or she has to take the trouble of operating the data-processing system to locate the step in which the error has occurred, identify the cause of the error and solve the problem.

SUMMARY OF THE INVENTION

To solve the above-described problems, the present invention provides a data-processing system having the functions of performing a step-by-step sequence of data-processing tasks and displaying the result of each task, on the basis of measurement data obtained with a measurement device, which includes:

an error detector for detecting an error if a certain data-processing task was incorrectly performed;

an error investigator for identifying the cause of the error detected by the error detector; and an error message displayer for displaying an error message showing the cause of the error identified by the error investigator, in response to a request for displaying the result of any of the aforementioned task and the subsequent tasks, if the error detector has detected an error.

The data-processing system according to the present invention may further include a guidance information displayer for creating a user interface through which users can select an error message and for displaying a guidance message containing information about the cause of the error relating to the selected error message and the procedure to remove the cause.

The data-processing system according to the present invention may further have the function of creating a user interface through which users can select the cause or the procedure to remove the cause shown in the guidance message and then displaying a setting screen relating to the selected cause or procedure if such a screen is available.

In the data-processing system for measurement devices according to the present invention, if one data-processing task has been incorrectly performed for some reason during the step-by-step data-processing sequence, the error detector detects the error, and the error investigator identifies the cause of the error. Then, the error message displayer prepares an error message indicating the reason why the data-processing task concerned was unsuccessful and then displays the error message as the result of each of the aforementioned task and the subsequent tasks. Therefore, even if the report created on a screen or a printing medium presents only the result of a specific data-processing task or the final result of the data-processing operation, the user can identify the step in which the error has occurred and learn the cause of the error. Thus, the user can identify and solve the problem in a shorter period of time.

In a mode of the present invention, when an error message is selected through the input unit, the guidance information displayer displays a guidance message containing information about the cause of the error relating to the selected error message and the procedure to remove the cause. The guidance message enables the problem to be solved with high possibility even if the user is unfamiliar with the measurement or data-processing operation.

In another mode of the present invention, when the user selects the cause of the error relating to the selected error message and the procedure to remove the cause shown in the guidance message, the data-processing system displays a setting screen relating to the selected cause or procedure. This mechanism enables the problem to be solved in an easier and quicker fashion.

BRIEF DESCRIPTION OF THE DRAWINGS

FIG. 1 shows the overall construction of an analysis system using a data-processing system as an embodiment of the present invention.

FIG. 2 shows an example of the quantitative determination report displayed by the data-processing system according to the present invention.

FIG. 3 shows an example of the guidance message.

FIG. 4 shows an example of the conventional quantitative determination report.

EXPLANATION OF NUMERALS

1 . . . Liquid Chromatograph Analyzer (LC Analyzer)
10 . . . Measurement Unit
11 . . . Liquid Supply Unit
12 . . . Sample Injection Unit
13 . . . Column Oven
14 . . . Detector
15 . . . Controller
20 . . . Data-Processing Unit
21 . . . Central Processing Unit (CPU)
22 . . . External Memory Unit
23 . . . Input Unit
24 . . . Display Unit
25 . . . Printer
30 . . . Data-Processing System For Measurement Devices
31 . . . Error Detector
32 . . . Error Investigator
33 . . . Error Message Displayer
34 . . . Guidance Information Displayer

DETAILED DESCRIPTION OF A PREFERRED EMBODIMENT

An embodiment of the data-processing system for measurement devices according to the present invention is described with reference to the attached drawings. FIG. 1 shows the overall construction of an analysis system using the data-processing system of the present embodiment. In the present example, the measurement device is a liquid chromatograph analyzer (called a "LC analyzer" hereinafter). It should be noted that the present invention can be used for other types of measurement devices.

The LC analyzer 1 consists of a measurement unit 10 for performing a measurement on a sample to acquire measurement data and a data-processing unit 20.

The measurement unit 10 includes a liquid supply unit 11, a sample injector 12, a column oven 13 and a detector 14. These components are operated by a controller 15 on the basis of the instructions from the data-processing unit 20. The measurement unit 10 corresponds to the measurement device in the present invention.

The data-processing unit 20 actually consists of a personal computer having a central processing unit (CPU) 21, an external memory unit 22, such as a semiconductor memory or a hard disk drive, an input unit 23 including a keyboard and/or a mouse, a display unit 24 including a cathode ray tube (CRT) or a liquid crystal display (LCD), and a printer 25.

The data-processing system for measurement devices according to the present invention is typically a set of software functions realized by commanding the CPU 21 to run an application program installed in the data-processing unit 20. It performs various kinds of data-processing tasks on a step-by-step basis, using the measurement data received from the measurement unit 10. The data-processing system 30, which is detailed later, has an error detector 31, an error investigator 32, an error message displayer 33 and a guidance information displayer 34. Typically, these functions are also realized by the CPU 21 running a specific application program.

To start an analysis with the LC analyzer 1, the user should first operate the input unit 23 to enter the necessary information, such as the analysis conditions and the data-processing conditions. On the basis of the conditions set by the user, the CPU 21 conducts the analysis by controlling the components of the measurement unit 10 through the controller 15. More specifically, the liquid supply unit 11 sends an eluting solution to the sample injector 12, which injects a liquid sample into the eluting solution. Then, the solution is transferred to the column contained in the column oven 13. While the solution is passing through the column, the solution is separated into its components, which reach the detector 14 at different points in time. Upon detecting each component, the detector 14 produces a signal corresponding to the component. The controller 15 receives this signal and sends it to the data-processing unit 20.

Upon receiving the signal, the CPU 21 of the data-processing unit 20 performs a sequence of data-processing tasks, e.g. peak integration, identification, calibration, quantitative determination, and statistical calculation, using the received signal. The CPU 21 also performs various operations in response to a manual request received through the input unit 23 or an automatic request issued by the program. For example, the CPU 21 can display the result of each data-processing task on the display unit 24. It can also print out a report showing the final results of the data-processing operation with the printer 25.

The data-processing operation can be incorrectly finished due to some trouble encountered during the process. Such an error is detected by the error detector 31. The error detector 31 may be mechanically constructed using electronic circuits and other elements instead of the software programs mentioned earlier.

Subsequent to the detection of an error by the error detector 31, the error investigator 32 identifies the cause of the error. In the present embodiment, a database showing the relationship between typical errors and their causes is created in the external memory unit 22, and the error investigator 32 searches this database for the cause related to the error encountered.

When a request for displaying the result of the data-processing operation is received through the input unit 23 or (automatically) issued by the program, the CPU 21 checks whether the error detector 31 has detected an error and the error investigator 32 has identified the cause of the detected error. If an error has been detected, the CPU 21 commands the error message displayer 33 to prepare an error message consisting of a character string, an image and/or other informative elements showing the cause of the error identified by the error investigator 32. This error message is displayed as the result of each of the current and subsequent data-processing tasks.

In a step-by-step data-processing sequence, a failure in one data-processing step also prevents the subsequent steps from producing correct results. However, an error that has occurred in the data-processing operation for one sample does not always affect the data-processing operation for another sample. In such a case, the latter operation can be performed without any problem. Therefore, it is not necessary to use the previous error message in the latter operation.

FIG. 2 shows a quantitative determination report, which is an example of a report showing the process results. This is an example of the report displayed or printed by the data-processing system according to the present invention using the measurement data that is used to create the erroneous quantitative determination report shown in FIG. 4. In FIG. 2, an error message of "No calibration curve is prepared" is displayed in the area for showing the result of the "Concentration" step for Methyl_paraben of ID number 1, in which the process was incorrectly performed.

For the Ethyl_paraben of ID number 2, another error message of "No peak is detected" is displayed in each of the areas for showing the results of the "Retention time" step and subsequent steps, instead of the zeros shown in FIG. 4.

With the report shown in FIG. 2, the user can immediately learn the reason why the data processing was unsuccessful. Even when a report of the result of only one step (e.g. the "Area") is shown on the display unit 24 or printed out through the printer 25 instead of the report shown in FIG. 2 informing the user of the results of the multiple steps, the user can immediately learn the cause of the error.

The error message clarifies the reason why the data-processing task was unsuccessful. However, this message is not necessarily enough for the user to know how to deal with the error. The guidance information displayer 34 of the data-processing system 30 helps the user in such a situation.

When the user selects an error message by operating the input unit 23, the guidance information displayer 34 displays a guidance message on the display unit 24. This message contains information about the cause of the error relating to the selected error message and the procedure to remove the cause.

For example, if the user operates the mouse to double-click on the error message "No calibration curve is prepared" in the quantitative determination report shown on the display unit 24, the CPU 21 (or the guidance information displayer 34) displays a guidance message shown in FIG. 3 on the display unit 24.

The guidance message shown in FIG. 3 contains two possible reasons why "No calibration curve is prepared", as follows:

"The operation necessary for creating a calibration curve using standard samples has not been finished"
"In the course of the analysis using the standard samples, the calibration curve was not correctly created."
This guidance message helps the user to make an estimation of the cause of the error.

For the item "The operation necessary for creating a calibration curve using standard samples is unfinished", the message also enumerates two possible procedures for solving the problem, as follows:

"Select <Batch Table> in <LC Postrun analysis> to execute a batch process for creating a calibration curve."
"Select <Calibration Curve> in <LC Postrun analysis> to create a calibration curve."
This information helps the user to learn effective methods for solving the problem.

To make the present system more useful, the guidance message also contains links for displaying detailed information about the methods for solving the problem. In FIG. 3, the links are set at the underlined text strings "How to create a calibration curve by the batch process" and "How to create a calibration curve through the Calibration Curve window." When the user clicks on one of the underlined text strings with the mouse, the guidance information displayer 34 shows detailed instructions on the screen.

It is also preferable to construct the present system so that it creates a guidance message screen that not only shows the method for solving the problem but also provides a link for directly displaying a setting screen on which the user can actually change the settings to solve the problem. In this process, the CPU 21 operates as follows:

For example, if the user has selected the error message "No peak is detected" through the input unit 23, the CPU 21 displays two possible causes of the error, as follows:
"Detection process failed due to inappropriate settings of peak integration parameters."
"Detection failed due to inappropriate settings of retention times and bandwidths in the compound table."

If the user selects the first item of information through the input unit 23, the CPU 21 displays a peak integration parameters setting screen. On the other hand, if the user selects the second item of information through the input unit 23, the CPU 21 displays a compound table setting screen.

This construction helps the user to solve the problem more quickly.

Finally, it should be noted that the above-described embodiment of the data-processing system for measurement devices according to the present invention is a mere example and can be changed or modified according to necessity within the spirit and scope of the present invention.

For example, the data-processing system may be embodied as an independent system to be externally connected to the measurement device; the data-processing system in the previous embodiment was built in the analysis system consisting of the measurement unit and the data-processing unit.

What is claimed is:

1. A data-processing system having functions of performing a step-by-step sequence of data-processing tasks and displaying a result of each task, on a basis of measurement data obtained with a liquid chromatograph, a gas chromatograph, or a mass spectrometer, comprising:
    an error detector for detecting an error if a certain data-processing task was incorrectly performed on the measurement data from the liquid chromatograph, the gas chromatograph, or the mass spectrometer;
    an error investigator for identifying a cause of the error detected by the error detector; and
    an error message displayer for displaying an error message showing the cause of the error identified by the error investigator, as the result of each of the aforementioned task and subsequent tasks in the sequence of data-processing tasks, in response to a request for displaying the result of any of the aforementioned task and the subsequent tasks, if the error detector detected an error.

2. The data-processing system according to claim 1, further comprising a guidance information displayer for creating a user interface through which users can select an error message and for displaying a guidance message containing information about the cause of the error relating to the selected error message and a procedure to remove the cause.

3. The data-processing system according to claim 2, further comprising a function of creating a user interface through which users can select the cause or the procedure to remove the cause shown in the guidance message and then displaying a setting screen relating to the selected cause or procedure if such a screen is available.

4. A data-processing method for controlling a data-processing system having functions of performing a step-by-step sequence of data-processing tasks and displaying a result of each task, on a basis of measurement data obtained with a liquid chromatograph, a gas chromatograph, or a mass spectrometer, said method comprising the steps of:

detecting an error, as the result of each of the aforementioned task and subsequent tasks in the sequence of data-processing tasks, if a certain data-processing task has been incorrectly performed on the measurement data from the liquid chromatograph, the gas chromatograph, or the mass spectrometer;

identifying a cause of the error detected; and displaying an error message showing the cause of the error in response to a request for displaying the result of any of the aforementioned task and subsequent tasks, if an error was detected.

5. The data-processing method according to claim 4, further including steps of creating a user interface through which users can select an error message and displaying a guidance message containing information about the cause of the error relating to the selected error message and a procedure to remove the cause.

* * * * *